United States Patent [19]

Padget et al.

[11] Patent Number: 5,043,098

[45] Date of Patent: Aug. 27, 1991

[54] A NON-IONIC DISPERSING AGENT

[75] Inventors: John C. Padget, Cheshire; David A. Pears, Chester; Stephen G. Yeates, Macclesfield, all of England; Gerardus C. Overbeek, Sprang-Capelle, Netherlands

[73] Assignee: Imperial Chemical Industries PLC, London, Great Britain

[21] Appl. No.: 273,091

[22] Filed: Nov. 18, 1988

[30] Foreign Application Priority Data

Nov. 18, 1987 [GB] United Kingdom ............... 87-26969
Nov. 18, 1987 [GB] United Kingdom ............... 87-26970

[51] Int. Cl.$^5$ .................. C08G 18/10; C08G 18/70
[52] U.S. Cl. ..................... 252/357; 252/351; 252/182.14; 252/182.17; 252/182.2; 524/839
[58] Field of Search ............ 252/357, 351; 524/839

[56] References Cited

U.S. PATENT DOCUMENTS

| | | |
|---|---|---|
| 2,653,932 | 9/1953 | Schwartz ............... 252/357 |
| 3,125,517 | 3/1964 | Voda ..................... 252/357 |
| 3,206,512 | 9/1965 | Koebner ................ 252/357 |
| 3,255,253 | 6/1966 | Kuryla . | 
| 3,454,646 | 7/1969 | Patton et al. ........... 252/357 |
| 4,235,811 | 11/1980 | Schulze et al. . |
| 4,529,744 | 7/1985 | Wood .................... 252/357 |
| 4,568,354 | 2/1986 | Davis et al. ............ 252/357 |

FOREIGN PATENT DOCUMENTS 420545 11/1934 United Kingdom ............... 252/357

Primary Examiner—John Kight, III
Assistant Examiner—Dennis R. Daley
Attorney, Agent, or Firm—Cushman, Darby & Cushman

[57] ABSTRACT

A nonionic dispersing agent suitable for use in the production of aqueous polyurethane dispersions, said agent having the formula:

$$R^1O(CH_2CHO)_m-(CO)_n-Z-N{\overset{R^3}{\underset{R^4}{\diagup\hspace{-1.5mm}\diagdown}}}$$
$$\phantom{R^1O(CH_2CH}\underset{R^2}{|}$$

wherein
R$^1$ represents a monovalent hydrocarbon radical containing 1-12 carbon atoms;
R$^2$ represents hydrogen or a mixture thereof with methyl and/or ethyl, at least 40% of the R$^2$ substituents in said mixture being hydrogen;
R$^3$ represents an isocyanate-reactive organic radical;
R$^4$ represents H or an isocyanate-reactive organic radical;
Z represents an alkylene radical containing 2-4 carbon atoms;
m is an integer from 5 to 150, and
n is 0 or 1.

13 Claims, No Drawings

A NON-IONIC DISPERSING AGENT

This invention relates to nonionic dispersing agents useful in the production of nonionic water-dispersible polyurethanes, to the water-dispersible polyurethanes and to the derived aqueous polyurethane dispersions.

Aqueous polyurethane dispersions are well known and are employed in the production of useful polyurethane products for example coatings and films. Dispersion of the polyurethane in the aqueous system has been achieved by the use of either external or internal dispersing or emulsifying agents but, in general, the internal agents, which can be ionic or nonionic, have been found to be more satisfactory.

Water-dispersible polyurethanes of nonionic character generally owe their dispersibility to the presence of pendent polyoxyethylene chains along the main polyurethane backbone, methods for the incorporation of such chains having been described in, for example, U.S. Pat. Nos. 3,905,929 and 3,920,598.

In the process described in U.S. Pat. No. 3,905,929, diols having polyethylene oxide side chains are prepared by reacting an organic diisocyanate with a polyethylene glycol mono-ether to form a monoisocyanate containing polyethylene oxide units which is then reacted in stoichiometric proportions with a dialkanolamine. The resulting diols, together with conventional diols, are then reacted with diisocyanates to form polyurethanes which, because of the pendent polyoxyethylene chains, are water-dispersible.

In the process described in U.S. Pat. No. 3,920,598, diisocyanates having polyethylene oxide side chains are prepared by reacting two moles of a diisocyanate with one mole of a polyethylene glycol monoether, the initially formed urethane monoisocyanate then being reacted at a higher temperature with the excess diisocyanate to form an allophanate diisocyanate having a pendent polyoxyethylene chain. Corresponding biuret diisocyanates are also described. The allophanate or biuret diisocyanates, together with conventional diisocyanates, are then reacted with diols to form polyurethanes which, because of the pendent polyoxyethylene chains, are water-dispersible.

Neither of these methods of making dispersing agents for incorporation into polyurethanes is completely satisfactory however because of the need to use expensive diisocyanates and because of the formation of undesirable by-products.

It has now been found that certain novel polyoxyalkylene amines as hereinafter described are excellent dispersing agents and may be incorporated into polyurethanes to provide water-dispersibility. The said polyoxyalkylene amines can be prepared from relatively low cost materials and they can be used at lower levels than the above mentioned prior art dispersing agents. Furthermore, the dispersions obtained are more stable than the prior art dispersions over a range of conditions.

Accordingly, the invention provides nonionic dispersing agents having the general formula:

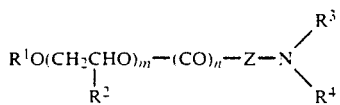

wherein
R$^1$ represents a monovalent hydrocarbon radical containing 1-12 carbon atoms;
R$^2$ represents hydrogen or a mixture thereof with methyl and/or ethyl, at least 40% of the R$^2$ substituents in said mixture being hydrogen,
R$^3$ represents an isocyanate-reactive organic radical;
R$^4$ represents H or an isocyanate-reactive organic radical;
Z represents an alkylene radical containing 2-4 carbon atoms;
m is an integer from 5 to 150, and
n is 0 or 1.

Examples of monovalent hydrocarbon radicals which may be represented by R$^1$ include C$_1$ to C$_{12}$ alkyl radicals, C$_4$ to C$_8$ cycloalkyl radicals, C$_6$ to C$_{15}$ aryl radicals and C$_7$ to C$_{10}$ aralkyl radicals. Preferably, R$^1$ is a C$_1$ to C$_4$ alkyl radical, especially methyl.

The identity of R$_2$ is such that the —CH$_2$CHR$^2$O— units are oxyethylene units or a mixture of oxyethylene units with oxypropylene and/or oxybutylene units, at least 40% of said units being oxyethylene. When a mixture of such units is present, they may be arranged randomly or in blocks. It is preferred that at least 60% of the oxyalkylene units are oxyethylene units.

The radical represented by R$^3$ (and R$^4$ when not hydrogen) is an organic radical containing an isocyanate-reactive group, for example —OH, —SH, —COOH, —PO$_3$H$_2$ and —NHR in which R represents hydrogen or optionally substituted alkyl. As specific examples of isocyanate-reactive radicals, there may be mentioned hydroxyalkyl, hydroxyalkoxyalkyl, hydroxy(polyalkyleneoxy) alkyl and hydroxyalkoxycarbonyl alkyl.

The alkylene radical represented by Z may be an ethylene, trimethylene, 1,2-propylene or butylene radical.

It is preferred that m is an integer in the range from about 10 to about 70.

One class of nonionic dispersing agents within the general class defined by Formula I has the formula:

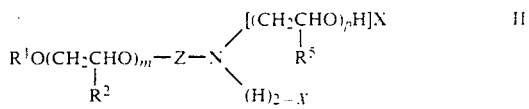

wherein R$^1$, R$^2$, Z and m have the meanings given above; R$^5$ represents hydrogen, methyl or ethyl; p is an integer from 1 to 100, and x is 1 or 2.

In the compounds of Formula II, it is preferred that Z is a 1,2-propylene radical wherein the secondary carbon atom is attached to the nitrogen atom. It is also preferred that R$^5$ is hydrogen and that p is 1.

The compounds of Formula I may be prepared by reacting a primary amine of the formula:

with at least one alkylene oxide of the formula:

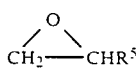

wherein $R^1$, $R^2$, $R^5$, Z and m have the meanings given above, at least 40% of the $R^2$ substituents being hydrogen.

The reaction between the primary amine and the alkylene oxide may be performed under standard oxyalkylation conditions. Thus, temperatures of from about 80° C. to 180° C. may be employed and alkaline catalysts may be used if necessary, for example when adding more than two moles of alkylene oxide per amino group.

Primary amines of Formula III are commercially available. Examples of such amines wherein Z is 1,2-propylene are the Jeffamine polyoxyalkyleneamines available from the Texaco Chemical Company. Amines wherein Z is trimethylene may be obtained by the cyanoethylation of polyalkylene glycol mono-ethers followed by hydrogenation.

The alkylene oxide of Formula IV is preferably ethylene oxide.

A second class of nonionic dispersing agents within the general class defined by Formula I has the formula:

$$R^1O(CH_2CHO)_mZN \diagup_{(H)_{2-x}}^{(CH_2CH-Q-T-XH)_x} \quad V$$
$$\phantom{R^1O(CH_2CHO)_m}|\phantom{ZN\diagup_{(H)_{2-x}}^{(CH_2CH)}} |$$
$$\phantom{R^1O(CH_2CHO)_m}R^2 \phantom{ZN\diagup_{(H)_{2-x}}^{(CH_2CH)}} R^6$$

or $$[R^1O(CH_2CHO)_mZNHCH_2CHQ]_2T \quad VI$$
$$\phantom{[R^1O(CH)}|\phantom{ZNHCH_2CHQ]_2T}|$$
$$\phantom{[R^1O(CH)}R^2\phantom{ZNHCH_2CHQ]_2T}R^6$$

wherein $R^1$, $R^2$ Z, m and x have the meanings given above;

$R^6$ represents hydrogen, halogen or $C_{1-4}$-alkyl:

Q represents a divalent electron-withdrawing group,

T presents a divalent hydrocarbon radical which may carry substituents or contain hetero atoms, and XH represents an isocyanate-reactive group.

In the compounds of Formula V and Formula VI, it is preferred that Z is a 1,2-propylene radical wherein the secondary carbon atom is attached to the nitrogen atom.

Halogen atoms which may be represented by $R^6$ in the compounds of Formulae V and VI include chlorine but it is preferred that $R^6$ is hydrogen or methyl.

Examples of electron withdrawing groups which may be represented by Q include —CO—, —COO—, SO—, SOO—, $SO_2O$ and CONR in which R is hydrogen or alkyl.

Hydrocarbon radicals which may be represented by T include alkylene, arylene and mixtures thereof, said radicals optionally carrying substituents or containing hetero-atoms. Examples of suitable radicals include alkylene radicals containing from 1 to 12 carbon atoms, oxyalkylene and polyoxyalkylene radicals of the formula —$(CH_2CHR^2O)$— wherein $R^2$ is as defined above and is from 1 to 10, phenylene and diphenylene radicals and other arylene radicals such as wherein Y is —O—, —S—, —$CH_2$—, —CO— or —$SO_2$—

Isocyanate-reactive groups which may be represented by —XH in the compounds of Formula V include —OH, —SH, —COOH, —$PO_3H_2$ and —NHR in which R represents hydrogen or an alkyl radical.

The compounds of Formula V may be prepared by reacting one mole of a primary amine of Formula III with one or two moles of an unsaturated compound of the formula:

$$CH_2=CH-Q-T-XH \quad VII$$
$$\phantom{CH_2=CH}|$$
$$\phantom{CH_2=CH}R^6$$

wherein $R^6$, Q, T and XH are as defined above.
by

The compounds of Formula VI may be prepared reacting one mole of a primary amine of Formula III with one half mole of an unsaturated compound of the formula:

$$CH_2=C-Q-T-Q-C=CH_2 \quad VIII$$
$$\phantom{CH_2=}|\phantom{Q-T-Q-}|$$
$$\phantom{CH_2=}R^6\phantom{Q-T-Q-}R^6$$

wherein $R^6$, Q and T are as defined above.

The reaction between the primary amine of Formula III and the unsaturated compound of Formula VII or Formula VIII may be performed under standard Michael addition conditions, solvents being used where necessary. Examples of unsaturated compounds of Formula VII particularly include 2-hydroxyethyl and 2-hydroxypropyl acrylates and methacrylates.

Examples of unsaturated compounds of Formula VIII especially include diacrylates and dimethacrylates wherein T is a $C_{4-10}$- alkylene residue, a polyoxyalkylene residue or an oxyethylated Bisphenol A residue.

A third class of nonionic dispersing agents within the general class defined by Formula I has the formula:

$$R^1O(CH_2CHO)_mCOZN \diagup_{R^4}^{R^3} \quad IX$$
$$\phantom{R^1O(CH_2CHO)_m}|$$
$$\phantom{R^1O(CH_2CHO)_m}R^2$$

wherein $R^1$, $R^2$, $R^3$, $R^4$ Z and m are as defined above.

In the compounds of Formula IX, it is preferred that Z is an ethylene radical or a 1,2-propylene radical wherein the secondary carbon atom is attached to the carbonyl group. It is also preferred that $R^3$ is hydroxyethyl or hydroxypropyl and that $R^4$ is selected from hydrogen, hydroxyethyl and hydroxypropyl. The compounds of Formula IX may be prepared by reacting an unsaturated ester of the formula:

$$R^1O(CH_2CHO)_mCOC=CH_2$$
$$\phantom{R^1O(CH)}|\phantom{mCOC=CH_2}|$$
$$\phantom{R^1O(CH)}R_2\phantom{mCOC=CH_2}R^7$$

wherein $R^1$, $R^2$ and m are as defined above and $R^7$ represents hydrogen, halogen or $C_{1-4}$- alkyl, with a primary or secondary amine of the formula:

$$R^3R^4NH \quad XI$$

wherein $R^3$ and $R^4$ are as defined above.

Compounds of Formula X may be obtained by reacting a polyglycol mono-ether of the formula:

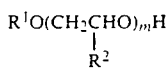     XII wherein $R^1$, $R^2$ and m are as defined above with an unsaturated acid of the formula:

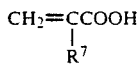     XIII wherein $R^7$ is as defined above, or with an ester-forming derivative thereof, for example a lower alkyl ester of said acid using ester interchange conditions. Ester-forming derivatives of acids of Formula XIII which may be used in the preparation of unsaturated esters of Formula X include the methyl and ethyl esters of acrylic and methacrylic acids.

Amines of Formula XI which may be used in the preparation of nonionic dispersing agents of Formula IX include isopropanolamine and di-isopropanolamine and, especially, ethanolamine and diethanolamine.

The dispersing agents of the invention may be used in the preparation of nonionic water-dispersible polyurethane prepolymers.

Thus, in a second aspect of the invention, there is provided a nonionic, water-dispersible, isocyanate-terminated polyurethane prepolymer comprising the reaction product of:

(i) an organic polyisocyanate;
(ii) at least one organic polyol having a molecular weight in the range 62 to 6000, and
(iii) a dispersing agent of Formula I.

The polyisocyanate used in making the prepolymer may be an aliphatic, cycloaliphatic, araliphatic or aromatic polyisocyanate. Examples of suitable polyisocyanates include ethylene diisocyanate, 1,6-hexamethylene diisocyanate, isophorone diisocyanate, cyclohexane-1,4-diisocyanate, 4,4'-dicyclohexylmethane diisocyanate, p-xylylene diisocyanate, 1,4-phenylene diisocyanate, 2,4-toluene diisocyanate, 2,6-toluene diisocyanate, 4,4'-diphenylmethane diisocyanate, 2,4'-diphenylmethane diisocyanate, polymethylene polyphenyl polyisocyanates and 1,5-naphthylene diisocyanate. Mixtures of polyisocyanates can be used and also polyisocyanates which have been modified by the introduction of urethane, allophanate, urea, biuret, carbodiimide, uretonimine or isocyanurate residues.

Organic polyols having molecular weights in the range 62-6000 which may be used in the preparation of the prepolymer particularly include diols and triols and mixtures thereof but higher functionality polyols may be used, for example as minor components in admixture with diols. The polyols may be polymeric polyols having molecular weights in the range 400 to 6000 or low molecular weight polyols having molecular weights below 400 depending upon the degree of flexibility desired in the final product. Mixtures of polymeric and/or low molecular weight polyols may be used.

The polymeric polyols may be members of any of the chemical classes of polymeric polyols used or proposed to be used in polyurethane formulations. In particular, they may be polyesters, polyesteramides, polyethers, polythioethers, polycarbonates, polyacetals, polyolefins or polysiloxanes. Preferred molecular weights are from 700 to 3000.

Polyester polyols which may be used include hydroxyl-terminated reaction products of polyhydric alcohols such as ethylene glycol, propylene glycol, diethylene glycol, neopentyl glycol, 1,4-butanediol, furan dimethanol, cyclohexane dimethanol, glycerol, trimethylolpropane, triethanolamine or pentaerythritol or mixtures thereof, with polycarboxylic acids, especially dicarboxylic acids or their ester-forming derivatives, for example succinic, glutaric and adipic acids or their methyl esters, phthalic anhydride or dimethyl terephthalate. Polyesters obtained by the polymerisation of lactones, for example caprolactone, in conjunction with a polyol may also be used. Polyesteramides may be obtained by the inclusion of amino-alcohols such as ethanolamine in polyesterification mixtures.

Polyether polyols which may be used include products obtained by the polymerisation of a cyclic oxide, for example ethylene oxide, propylene oxide or tetrahydrofuran or by the addition of one or more such oxides to polyfunctional initiators, for example water, ammonia, ethylene glycol, propylene glycol, diethylene glycol, cyclohexane dimethanol, glycerol, trimethylolpropane, pentaerythritol, triethanolamine, aniline, ethylene diamine, toluene diamine, diaminodiphenylmethane, polymethylene polyphenylene polyamines or Bisphenol A. Especially useful polyethers include polyoxypropylene diols and triols, poly(oxyethylene-oxypropylene) diols and triols obtained by the simultaneous or sequential addition of ethylene and propylene oxides to appropriate initiators and polytetramethylene ether glycols obtained by the polymerisation of tetrahydrofuran.

Polythioether polyols which may be used include products obtained by condensing thiodiglycol either alone or with other glycols, dicarboxylic acids, formaldehyde, aminoalcohols or aminocarboxylic acids.

Polycarbonate polyols which may be used include products obtained by reacting diols such as 1,3-propanediol, 1,4-butanediol, 1,6-hexanediol, diethylene glycol or tetraethylene glycol with diaryl carbonates, for example diphenyl carbonate, or with phosgene.

Polyacetal polyols which may be used include those prepared by reacting glycol or hexanediol with formaldehyde. Suitable polyacetals may also be prepared by polymerising cyclic acetals.

Suitable polyolefin polyols include hydroxy-terminated butadiene homo and copolymers.

Organic polyols having molecular weights below 400 which may be used in the preparation of the prepolymer particularly include diols and triols and mixtures thereof but higher functionality polyols may be used. Examples of such lower molecular weight polyols include ethylene glycol, diethylene glycol, 2,2-dimethylolpropionic acid, tetraethylene glycol, bis(hydroxyethyl) terephthalate, cyclohexane dimethanol, furan dimethanol, glycerol, triethanolamine and the reaction products, up to molecular weight 399, of such polyols with propylene oxide and/or ethylene oxide.

The non-ionic, water dispersible isocyanate-terminated polyurethane prepolymer may be prepared in conventional manner by reacting a stoichiometric excess of the organic polyisocyanate with at least one organic polyol having a molecular weight in the range 62 to 6000 and the dispersing agent of Formula I under substantially anhydrous conditions at a temperature between about 30° C. and about 130° C. until reaction between the isocyanate groups and the hydroxyl groups is substantially complete. The polyisocyanate and the active hydrogen containing components are suitably reacted in such proportions that the ratio of number of isocyanate groups to the number of hydroxyl groups is in the range form about 1.1:1 to about 6:1, preferably within the range of from 1.5:1 to 3:1.

The dispersing agent of Formula I is suitably used in such proportions that the polyurethane prepolymer contains from 2 to 30%, preferably from 5 to 20%, by weight of side chain polyethylene oxide segments.

If desired, catalysts such as dibutyltin dilaurate and stannous octoate may be used to assist prepolymer formation and a non-reactive solvent may be added before or after prepolymer formation to control the viscosity. Suitable solvents which may be used include acetone, methylethylketone, dimethylformamide, ethylene carbonate, propylene carbonate, diglyme, N-methylpyrrolidone, ethyl acetate, ethylene and propylene glycol diacetates, alkyl ethers of ethylene and propylene glycol monoacetates, toluene, xylene and sterically hindered alcohols such as t-butanol and diacetone alcohol. The preferred solvents are water-miscible solvents such as N-methylpyrrolidone, dimethyl sulphoxide and dialkyl ethers of glycol acetates or mixtures of N-methylpyrrolidone and methyl ethyl ketone.

The nonionic water-dispersible polyurethane prepolymers of the invention may be used in the preparation of aqueous polyurethane dispersions.

Thus, in a third aspect of the invention, there is provided an aqueous dispersion of a nonionic, water-dispersible polyurethane wherein the polyurethane is the reaction product of:
(a) a nonionic, water-dispersible, isocyanate-terminated polyurethane prepolymer formed by reacting:
  (i) an organic polyisocyanate;
  (ii) at least one organic polyol having a molecular weight in the range 62 to 6000, and
  (iii) a dispersing agent of Formula I; and
(b) an active hydrogen containing chain extender.

The aqueous dispersions of the invention may be prepared by dispersing the nonionic, water dispersible, isocyanate-terminated polyurethane prepolymer in an aqueous medium and chain extending the prepolymer with a active hydrogen containing chain extender.

The prepolymer may be dispersed in water using techniques well known in the art. Preferably, the prepolymer is added to the water with agitation or, alternatively, water may be stirred into the prepolymer.

The active hydrogen containing chain extender which is reacted with the prepolymer is suitably a polyol, an amino alcohol, ammonia, a primary or secondary aliphatic, alicyclic, aromatic, araliphatic or heterocyclic amine especially a diamine, hydrazine or a substituted hydrazine. Water-soluble chain extenders are preferred, and water itself may be effective.

Examples of suitable chain extenders useful herein include ethylene diamine, diethylene triamine, triethylene tetramine, propylene diamine, butylene diamine, hexamethylene diamine, cyclohexylene diamine, piperazine, 2-methyl piperazine, phenylene diamine, tolylene diamine, xylylene diamine, tris(2-aminoethyl) amine, 3,3'-dinitrobenzidine, 4,4'-methylenebis(2-chloroaniline), 3,3'-dichlorobenzidine, 2,6-diaminopyridine, 4,4'-diaminodiphenylmethane, menthane diamine, m-xylene diamine and isophorone diamine. Also, materials such as hydrazine, azines such as acetone azine, substituted hydrazines such as, for example, dimethyl hydrazine, 1,6-hexamethylene-bis-hydrazine, carbodihydrazine, hydrazides of dicarboxylic acids and sulfonic acids such as adipic acid mono- or dihydrazide, oxalic acid dihydrazide, isophthalic acid dihydrazide, tartaric acid dihydrazide, 1,3-phenylene disulfonic acid dihydrazide, omega-amino-caproic acid dihydrazide, hydrazides made by reacting lactones with hydrazine such as gamma-hydroxybutyric hydrazide, bis-semi-carbazide, bis-hydrazide carbonic esters of glycols such as any of the glycols mentioned above.

Where the chain extender is other than water, for example a diamine or hydrazine, it may be added to the aqueous dispersion of prepolymer or, alternatively, it may already be present in the aqueous medium when the prepolymer is dispersed therein.

The chain extension can be conducted at elevated, reduced or ambient temperatures. Convenient temperatures are from about 5° to 95° C. or more, preferably from about 10° to about 45° C.

The amount of chain extender employed should be approximately equivalent to the free-NCO groups in the prepolymer, the ratio of active hydrogens in the chain extender to NCO groups in the prepolymer preferably being in the range from 1.0 to 2.0:1. Of course when water is employed as the chain extender, these ratios will not be applicable since the water, functioning both as chain extender and dispersing medium, will be present in a gross excess relative to the free NCO groups.

It will be appreciated by those skilled in the art that the nonionic, water-dispersible polyurethane may be either linear, branched or crosslinked in structure depending upon the components used in its formation. Polyurethanes having a degree of branching of up to one crosslink for each 3000 atomic weight units are of greatest interest.

The polyurethane may also, depending upon the components used, contain free acid or tertiary amino groups, such groups being crosslinkable in conventional manner. Particularly suitable acid groups are carboxylic acid groups. Any free acid or tertiary amino group content is suitably in the range from 5 to 180 milliequivalents per 100 g.

In a further variant, any free acid or tertiary amine groups present in the polyurethane may be converted to salt groups which enhance the water-dispersibility. Thus, polyurethanes containing carboxylic acid groups may be neutralised with, for example, tertiary amines so that the polyurethane has not only a nonionic but also an anionic hydrophilic centre. The production of carboxy-containing polyurethanes is well known in the art. Such polyurethanes as adapted by the present invention typically being derived from prepolymers comprising reaction products of:
  (i) an organic polyisocyanate;
  (ii) at least one organic polyol having a molecular weight in the range 62 to 6000,
  (iii) a dispersing agent of Formula I; and group containing diol or triol .
  (iv) a carboxy group containing diol or triol.
Suitable carboxy group containing diols and triol are well known and include dimethylolpropionic acid.

Polyurethanes containing not only a nonionic but also a cationic hydrophilic centre may also be prepared in known manner.

The aqueous dispersions of the invention may be advantageously employed as coating compositions, for which purpose they may be further diluted with water and/or organic solvents, or they may be supplied in more concentrated form by evaporation of water and- /or organic components of the liquid medium. As coating compositions, they may be applied to any substrate including wood, metals, glass, cloth, leather, paper, plastics, foam and the like, by any conventional method including brushing, dipping, flow coating, spraying and the like. The compositions may contain other conventional ingredients including organic solvents, pigments, dyes, emulsifiers, surfactants, thickeners, heat stabilizers, levelling agents, anti-cratering agents, fillers, sedimentation inhibitors, UV absorbers, antioxidants and the like introduced at any stage of the production process or subsequently. It is possible to include an amount of antimony oxide in the dispersions to enhance the fire retardant properties. The dispersions may also be used as adhesives for materials such as polypropylene, polyester, polyurethane, leather and the like or as binding agents for various particulate materials.

The dispersions, which suitably have solids contents of from about 20 to 60% by weight, preferably from about 25 to 50% by weight, are stable over a wide pH range (2–13) and are substantially unaffected by electrolytes.

Those products containing free acid groups, for example —COOH groups, can be reacted with melamines, polyisocyanates, carbodiimides, polyaziridines, polyepoxides or polyvalent metal ions, for example aluminium, magnesium, barium, beryllium, cobalt, lead, copper or antimony and especially zinc, zirconium or calcium. Similarly, products containing free tertiary amino groups may be reacted with polyhalogenated hydrocarbons so as to quaternise the amino groups. Suitable polyhalogenated hydrocarbons include $\alpha,\alpha'$-dichloro-1,4-xylene, $\alpha,\alpha'$-dichloro-1,2-xylene, 1,5-dibromopentane and 1,4-dibromobutane. The crosslinking reactions can take place at room temperature or can be accelerated by heat. The crosslinked polymers are thermoset in nature and have a high degree of solvent resistance.

If desired, the polyurethane dispersions of the invention may be used in admixture with other dispersions, for example dispersions of vinyl polymers and copolymers.

Thus, in a further aspect of the invention, there is provided an aqueous polymer dispersion containing a water dispersible polyurethane and a vinyl polymer, the polyurethane being the product of reacting
(a) a water-dispersible, isocyanate-terminated polyurethane prepolymer formed by reacting:
  (i) an organic polyisocyanate;
  (ii) at least one organic polyol having a molecular weight in the range 62 to 6000, and optionally a carboxy group containing diol or triol and
  (iii) a dispersing agent of Formula I; and
(b) an active hydrogen containing chain extender.

The aqueous polymer dispersions may be prepared by simply blending an aqueous dispersion of a water-dispersible polyurethane as described above with an aqueous dispersion of a vinyl polymer. It is preferred, however, to polymerise one or more vinyl monomers in the presence of the aqueous polyurethane dispersion. This may be effected by adding the vinyl monomer or monomers to the polyurethane dispersion, either gradually or all at once, and subjecting the monomer to polymerisation conditions during and/or after its addition to the dispersion. Alternatively, a solution of prepolymer in vinyl monomer may be dispersed in an aqueous medium after which the prepolymer is chain extended and the vinyl monomer polymerised.

Vinyl monomers which may be polymerised to form the vinyl polymer component of the aqueous dispersions of the invention include any radically polymerisable olefinically unsaturated compounds or mixtures thereof. Thus, there may be mentioned hydrocarbon monomers, for example butadiene, isoprene, styrene and divinyl benzene, acrylic and substituted acrylic monomers, for example acrylic and methacrylic acids, acrylonitrile, methyl, ethyl, 2-hydroxyethyl, butyl and isobutyl acrylates and methacrylates, acrylamide, methacrylamide, N-methylolacrylamide and other commonly used monomers such as vinyl chloride, vinylidene chloride, vinyl esters, vinyl ethers, vinyl ketones and heterocyclic vinyl compounds.

Polymerisation of the vinyl monomer or monomers may be effected using conventional polymerisation techniques. Thus, the monomer may be contacted with free radical initiators, especially initiators partitioned between the aqueous and organic phases, for example a combination of t-butylhydroperoxide, isoascorbic acid and Fe.EDTA or water-soluble initiators such as persulphates.

The weight ratio of polyurethane to vinyl polymer in the dispersions of the invention is suitably in the range from 9:1 to 1:9 with a solids content in the range from about 30% to about 45% by weight. Viscosities are usually between 20 and 1000 cps at 25° C. and the pH is commonly around 7.5 to 9.0.

The aqueous polymer dispersions may be utilised for purposes similar to those described for the nonionic polyurethane dispersions. Thus, they may be used as coating compositions, adhesives, binding agents and the like.

The invention is illustrated but not limited by the following Examples

Example 1

1307.6 g of a polyoxyalkyleneamine of the formula:

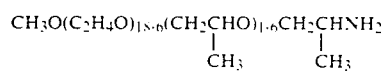

available from the Texaco Chemical Company as Jeffamine M-1000 was charged to a reactor and heated to 130° C. Ethylene oxide (65.5 ml) was added in one portion. The reaction was complete after 6 hours and the molten product having the structure:

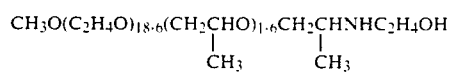

was then discharged from the reactor.

Example 2

100 g of Jeffamine M-1000 was reacted with ethylene oxide (40 ml) under the conditions described in Example 1. The reaction, which was complete after 12 hours, gave a product having the structure:

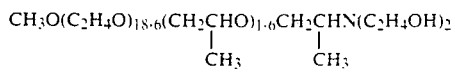

Example 3

A prepolymer solution was prepared for comparative purposes using a known dispersing agent. In the preparation, 46.2 g of isophorone diisocyanate, 101.4 g of polypropylene glycol of molecular weight 1200, 52.4 g of a dispersing agent (obtained by reacting 2 moles of isophorone diisocyanate with 1 mole of methoxypolyethylene glycol of molecular weight 750 and 1 mole of diethanolamine) and 85,7 g of N-methylpyrrolidone were charged to a stirred reaction flask under nitrogen at ambient temperature. The flask was then heated to 60°-65° C. and 1.66 g of dibutyltin dilaurate were added. The temperature was allowed to rise to 90° C. and was then maintained at 90°-95° C. for 2 hours. The prepolymer solution (NCO content 1.64%) was allowed to cool to 40°-45° C. and 205 g were added over 30 minutes to 500 g of stirred distilled water at 20-25° followed by 1.80 g hydrazine monohydrate. A 10° exotherm was observed, the dispersion then being stirred for 2 hours after which time it had cooled to 25° C. The product was designated Dispersion A.

Dispersions B and C were prepared in the same way as Dispersion A but replacing the dispersing agent by the dispersing agents described in Examples 1 and 2 respectively.

The three dispersions had the following properties.

|   | % Agent by weight in prepolymer | % Solids by weight | Particle Size (μm) |
|---|---|---|---|
| A | 26.2 | 19.4 | 0.115 |
| B | 24.3 | 19.4 | 0.044 |
| C | 25.1 | 18.8 | 0.038 |

The thermal stabilities of the dispersions were as follows:

|   | 40° C. | 60° C. | 80° C. |
|---|---|---|---|
| A | √ | X(20 min) | X(20 min) |
| B | √ | √ | √ |
| C | √ | √ | √ |

√ = no coagulation after 6 hours
X = coagulation before 6 hours

The particle size and thermal stability figures show that the dispersing agents of the invention have given finer and more stable dispersions than was given by the prior art agent.

Example 4

2-Hydroxyethyl acrylate (23.2 g, 0.2 mol) was added in one portion to a stirred solution of a polyoxyalkyleneamine of the formula:

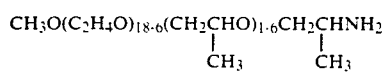

available from the Texaco Chemical Company as Jeffamine M-1000 (200 g, 0.2 mol) in toluene (400 ml) at 70° C. After 24 hours, the solvent was removed in vacuo at 50° C. to give a colourless waxy solid. Spectroscopic analysis confirmed the product to be the Michael addition adduct of the two starting materials.

Example 5

Tripropylene glycol diacrylate (10 g, 33 mmol) was added in one portion to a stirred solution of Jeffamine M-1000 (73.7 g, 74 mmol) in toluene (200 ml) at 70° C. After 24 hours, the solvent was removed in vacuo at 50° C. to give a colourless waxy solid. Spectroscopic analysis confirmed the product to be the Michael addition adduct of the two starting materials.

Example 6

A prepolymer solution was prepared for comparative purposes using a known dispersing agent. In the preparation, 46.2 g of isophorone diisocyanate, 101.4 g of polypropylene glycol of molecular weight 1200, 52.4 g of a dispersing agent (obtained by reacting 2 moles of isophorone diisocyanate with 1 mole of methoxypolyethylene glycol of molecular weight 750 and 1 mole of diethanolamine) and 85,7 g of N-methylpyrrolidone were charged to a stirred reaction flask under nitrogen at ambient temperature. The flask was then heated to 60°-65° C. and 1.66 g of dibutyltin dilaurate were added. The temperature was allowed to rise to 90° C. and was then maintained at 90°-95° C. for 2 hours. The prepolymer solution (NCO content 1.64%) was allowed to cool to 40°-45° C. and 205 g were added over 30 minutes to 500 g of stirred distilled water at 20°-25° followed by 1.80 g hydrazine monohydrate. A 10° exotherm was observed, the dispersion then being stirred for 2 hours after which time it had cooled to 25° C. The prepolymer used in the preparation of this dispersion contained 26.2% by weight of Agent A. Corresponding dispersions were prepared from prepolymers in which Agent A was replaced by the dispersing agents described in Examples 4 and 5 respectively (Agents B and C). The three dispersions had the following properties.

|   | % Agent by weight in prepolymer | % Solids by weight | Particle Size (μm) |
|---|---|---|---|
| A | 26.2 | 19.4 | 0.115 |
| B | 24.3 | 19.4 | 0.044 |
|   | 25.1 | 18.8 | 0.038 |

The thermal stabilities of the dispersions were as follows:

|   | 40° C. | 60° C. | 80° C. |
|---|---|---|---|
| A | √ | X(20 min) | X(20 min) |
| B | √ | √ | √ |
| C | √ | √ | √ |

√ = no coagulation after 6 hours
X = coagulation before 6 hours

Example 7

1000 g of a polyoxyalkyleneamine of the formula

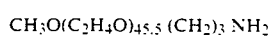

was charged to a reactor and heated to 130° C. Ethylene oxide (50 ml) was added in one portion. The reaction was complete after 6 hours and the molten product having the structure:

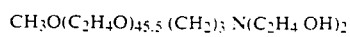

was discharged from the reactor.

Example 8

1000 g of a polyoxyalkyleneamine of the formula $$CH_3O(C_2H_4O)_{68}(CH_2)_3NH_2$$

was charged to a reactor and heated to 130° C. Ethylene oxide (34 ml) was added in one portion. The reaction was complete after 6 hours and the molten product having the structure:

$$CH_3O(C_2H_4O)_{68}(CH_2)_3N(C_2H_4OH)_2$$

was discharged from the reactor.

Example 9

465.7 g of a hydroxy acrylate of the formula:

$$CH_2=CHCOOC_2H_4O(CO(CH_2)_5O)_2H$$

available from the Union Carbide chemical company as TONE M-100 was added in one portion to stirred Jeffamine M-1000 (13549) at 70° C. The mixture was stirred and heated at 70° C. for a further 18 hours. The cooled product was a colourless waxy solid and was shown by spectroscopic analysis to be the Michael addition adduct of the two starting materials.

Example 10

198 g of 2-hydroxypropyl acrylate was added in one portion to stirred Jeffamine M-1000 (1520 g) at 80° C. After 18 hours at 80° C., the mixture was cooled to give a colourless waxy solid. The structure of the product was shown to be the Michael adduct of the two starting materials by spectroscopic analysis.

Example 11

1169 g of 2-hydroxyethyl acrylate was added in one portion to 2091 g of a polyoxyalkyleneamine of the formula:

$$CH_3O(C_2H_4O)_{45.5}(CH_2)_3NH_2$$

at 80° C. The mixture was stirred and heated at 80° C. for a further 18 hours The cooled product was a colourless waxy solid and was shown by spectroscopic analysis to be the Michael addition product of the two starting materials.

Example 12

A mixed non-ionically and anionically stabilised dispersion was prepared from a pre polymer solution using the dispersing urgent of structure:

$$CH_3O(C_2H_4)_{18.6}(CH_2CHO)_{1.6}CH_2CHNHCH_2CH_2COCH_2CH_2O\!-\!\!\!\!\underset{CH_3\ \ \ \ \ \ CH_3\ \ \ \ \ \ O}{|\ \ \ \ \ \ \ \ \ \ \ \ |\ \ \ \ \ \ \ \ \ \ \ \ \|}$$

In the preparation, 50.08 g of isophorone diisocyanate, 4.36 g of dimethylolpropionic acid, 67.59 g of polytetrahydrofuran of molecular weight 1000, 27.96 g of the above dispersing agent and 37.5 g of N-methylpyrrolidone were charged to a stirred reaction vessel under nitrogen at ambient temperature. The flask was then heated to 60°–65° C. and 1.8 g of dibutyltin dilaurate were added. The temperature was allowed to rise to 90° C. and was maintained at 90°–95° C. for 2 hours. The prepolymer solution was allowed to cool to 40°–45° C. and 3.29 g of triethylamine was added. 185 g of the prepolymer were added to 450 g of stirred water at 20°–25° C. followed by 4.41 g of hydrazine monohydrate. The dispersion had a particle size of 0.058 μm, contained 29% w/w solids and was stable to the addition of acid.

Example 13

A prepolymer solution was prepared using the diol dispersing agent of structure:

$$CH_3O(C_2H_4O)_{18.6}(CH_2CHO)_{1.6}CH_2CHN(C_2H_4OH)_2\!-\!\!\!\!\underset{CH_3\ \ \ \ \ \ CH_3}{|\ \ \ \ \ \ \ \ \ \ \ \ |}$$

In the preparation, 38.85 g of isophorone diisocyanate, 87.38 g of polytetrahydrofuran of molecular weight 1000, 23.77 g of the above mentioned dispersing diol and 64.29 g N-methylpyrrolidone were charged to a stirred reaction vessel under nitrogen at ambient temperature The flask was then heated to 60°–15° C. and 1.4 g of dibutyltin dilaurate were added. The temperature was allowed to rise to 90° C. and was then maintained at 90°–95° C. for 2 hours. The prepolymer solution (NCO content 1.76%) was allowed to cool to 40°–45° C. and 205 g were added over 30 minutes to 500 g of stirred distilled water at 20°–25° C. followed by 2.8 g of hydrazine monohydrate. A 10° exotherm was observed, the dispersion then being stirred for 2 hours after which time it had cooled to 25° C. The dispersion had a particle size of 0.135 μm and contained 29 w/w% solids.

Example 14

Preparation of :

$$MeO(C_2H_4O)_{22}CCH_2CH_2NHCH_2CH_2OH\!-\!\!\!\!\underset{O}{\|}$$

A 2 liter three-neck flask fitted with a mechanical stirrer, thermometer, air ebullator, a distillation head atop a metallised vacuum jacketed column was charged with 1000 g of polyethylene glycol methyl ether of molecular weight 1000, 240 g of methyl acrylate and 1.24 g of Topanol 0. The mixture was heated to reflux to remove residual water by azeotropic distillation. Tetraisopropyltitanate (6 g) was added and the solution maintained at reflux. The head temperature, initially at 80° C., dropped to 64° C. as methanol was generated. The distillation head was adjusted such that all the distillate was collected below 65° C. Once the theoretical amount of methanol had been removed, the mixture was vacuum stripped to remove unreacted methyl acrylate.

The mixture was cooled to 60° C. and 61 g of ethanolamine were added to the stirred mixture. The mixture was stirred and heated for a further 18 hours. The product on cooling was isolated as a waxy solid and was shown by spectroscopic techniques to be the Michael addition adduct of ethanolamine and the acrylate of polyethylene glycol methyl ether 100.

Example 15

Into a dry 3 necked round bottom flask under nitrogen was charged 8.07 g dimethylol propionic acid, 20.31 g of polypropylene glycol 1200, 31.50 g of the dispersing agent described in Example 4 (eq wt =558 gmol$^{-1}$), 40.12 g isophorone diisocyanate, 42.86 g N-methylpyrrolidone. The mixture was heated with agitation to 65°-70° C. and 1.44 g of dibutyltin dilaurate in NMP (10% w/w) was added. The reaction was seen to exotherm and was subsequently held at 90°-95° C. for 1 hour at which time a further 1.44 g of dibutyltin dilaurate in NMP was added. After a further 3 hours at temperature, the reaction was monitored by determination of the free isocyanate using the dibutyl amine method and was found to be complete (%NCO found =3.81, % NCO theoretical=3.90%).136.9 g of the above prepolymer was then dispersed in distilled water (212.86 g) over a 30 minute period (T prepolymer=60° C.-65° C.; T water=20° C.). Upon dispersion, 2.98 g of 64% hydrazine was added and a 10° C. exotherm noted. The dispersion had a solids content of 26.8%, particle size of 65nm and a pH =4.9.

The urethane-acrylate was prepared using a seed-batch technique. To a 500ml reactor flask under nitrogen was charged 75 g of the nonionic polyurethane prepared as described above, 1381 g distilled water and the temperature raised to 40° C. with agitation 1.61 g of a 1% ferrous sulphate solution (0.02 wt-% on total monomer) and 0.51 g triethylene tetramine were charged to the vessel. 8.04 g of a 1% solution of i-ascorbic acid (0.3 wt. % on monomer), 5.47 g of a 35% solution of t-butyl hydroperoxide solution (0.5 wt-% on monomer) and 18.76 g butyl acrylate with 8.84 g vinylidene chloride were added rapidly over a 5 minute period. An exotherm of 10.5° C. was observed. Once the temperature had fallen to 42° C. the addition of additional i-ascorbic acid solution, t-butyl hydroperoxide solution and monomer as outlined above was repeated and an exotherm of 8.8° C. observed. The procedure was repeated a third time with an exotherm of 7.2° C. being observed. The reaction was then held at 40° C. for a further 1 hour. The product was subsequently filtered (50 μm mesh) with <1 g of coagulum recovered. The resulting dispersion had a solids content of 29.1% w/w (% monomer conversion=97), a particle size of 260mm and a pH of 6.1

We claim:

1. A non-ionic dispersing agent having the general formula:

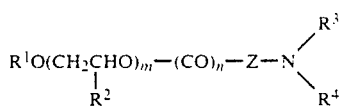

wherein
$R^1$ represents a a $C_1$-$C_4$ alkyl radical;
$R^2$ represents hydrogen or a mixture thereof with methyl and/or ethyl, at least 40% of the $R^2$ substituents in said mixture being hydrogen;
$R^3$ represents an isocyanate-reactive organic radical;
$R^4$ represents H or an isocyanate-reactive organic radical;
Z represents 1,2-propylene;
m is an integer from 5 to 150, and
n is 0 or 1.

2. A dispersing agent according to claim 1 wherein $R^1$ is methyl.

3. A dispersing agent according to claim 1 wherein at least 60% of the $R^2$ substituents are hydrogen atoms.

4. A dispersing agent according to claim 1 wherein $R^3$, and $R^4$ when not hydrogen, is an organic radical containing —OH, —SH, —COOH, —PO$_3$H$_2$ or —NHR in which R is hydrogen or optionally substituted alkyl.

5. A dispersing agent according to claim 4 wherein the hydroxy-containing organic radical is hydroxyalkyl or hydroxyalkoxycarbonylalkyl.

6. A dispersing agent according to claim 1 having the formula:

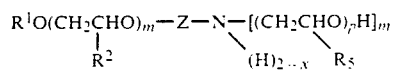

wherein
$R^1$, $R^2$, Z and m are as defined in claim 1;
$R^5$ represents hydrogen, methyl or ethyl;
p is an integer from 1 to 100, and x is 1 or 2.

7. A dispersing agent according to claim 6 wherein Z is a 1,2 polypropylene radical of which the secondary carbon atom is attached to the nitrogen atom.

8. A dispersing agent according to claim 1 having the formula:

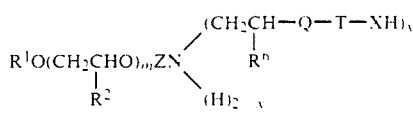

wherein
$R^1$, $R^2$, Z and m are as defined in claim 1;
$R^6$ represents hydrogen, halogen or $C_{1-4}$- alkyl;
Q represents a divalent electron-withdrawing group;
T represents a divalent hydrocarbon radical which may carry substituents or contain hetero atoms;
XH represents an isocyanate-reactive group, and x is 1 or 2.

9. A dispersing agent according to claim 1 having the formula:

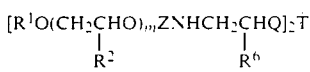

wherein $R^1$, $R^2$, $R^6$, Z, Q, T, and m are as defined in claim 8.

10. A dispersing agent according to claim 8 or claim 9 wherein Z is a 1,2-propylene radical of which the secondary carbon atom is attached to the nitrogen atom.

11. A dispersing agent according to any of claims 8 to 9 wherein $R^6$ is hydrogen or methyl.

12. A dispersing agent according to claim 1 having the formula:

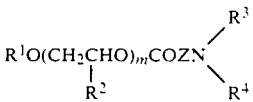

wherein $R^1$, $R^2$, $R^3$, $R^4$, Z and m are as defined in claim 1.

13. A dispersing agent according to claim 12 wherein $R^3$ is hydroxyethyl and $R^4$ is hydrogen or hydroxyethyl.

* * * * *

UNITED STATES PATENT AND TRADEMARK OFFICE
CERTIFICATE OF CORRECTION

PATENT NO.   : 5,043,098
DATED        : August 27, 1991
INVENTOR(S)  : PADGET et al It is certified that error appears in the above-indentified patent and that said Letters Patent is hereby corrected as shown below:

On the title page, Item [73]:Assignee: change "Imperial Chemical Industries, PLC, London, Great Britain" to --Imperial Chemical Industries PLC and ICI Resins BV, London, England and Waalwijk, Holland, respectfully--.

Signed and Sealed this

Twenty-ninth Day of March, 1994

Attest:

BRUCE LEHMAN

*Attesting Officer*  *Commissioner of Patents and Trademarks*